United States Patent [19]

Schirmer et al.

[11] Patent Number: 4,709,078
[45] Date of Patent: Nov. 24, 1987

[54] ACRYLATES, AND FUNGICIDES WHICH CONTAIN THESE COMPOUNDS

[75] Inventors: Ulrich Schirmer, Heidelberg; Stefan Karbach, Ludwigshafen; Ernst-Heinrich Pommer, Limburgerhof; Eberhard Ammermann, Ludwigshafen; Wolfgang Steglich, Bonn-Roettgen; Barbara A. M. Schwalge, Lohmar; Timm Anke, Kaiserslautern, all of Fed. Rep. of Germany

[73] Assignee: BASF Aktiengesellschaft, Ludwigshafen, Fed. Rep. of Germany

[21] Appl. No.: 865,406

[22] Filed: May 21, 1986

[30] Foreign Application Priority Data

May 30, 1985 [DE] Fed. Rep. of Germany ....... 3519282

[51] Int. Cl.$^4$ ............................................. C07C 69/76
[52] U.S. Cl. ..................... 560/060; 562/470; 514/543; 514/532; 514/570; 560/11; 560/12; 560/14; 560/23; 560/34; 560/21; 560/55; 560/56; 558/13; 558/414
[58] Field of Search ................... 560/60; 562/470; 514/543, 532, 570

[56] References Cited

FOREIGN PATENT DOCUMENTS 0044448 1/1982 European Pat. Off. ............ 69/734
178826 4/1986 European Pat. Off. .
1173722 1/1965 Fed. Rep. of Germany .

OTHER PUBLICATIONS

Schramm et al., "Strobilurin A und B, Antifungische Stoffwechselprodukte aus Strobilurus Tenacellus, Chemische Berichte, vol. 111, pp. 2779-2784.

Primary Examiner—Paul J. Killos
Attorney, Agent, or Firm—Keil & Weinkauf

[57] ABSTRACT

Acrylates of the general formula

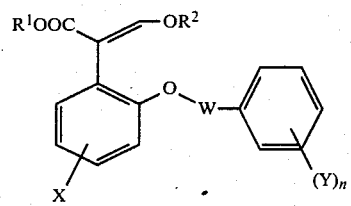

wherein $R^1$ and $R^2$ independently of one another are each $C_1-C_8$-alkyl, X is hydrogen, $C_1-C_4$-alkyl, halogen, $C_1-C_4$-alkoxy, haloalkyl, cyano or nitro, W is unsubstituted or alkyl-substituted, saturated or unsaturated $C_1-C_{10}$-alkylene, Y is hydrogen, alkyl, haloalkyl, alkoxyalkyl, cycloalkyl, aralkyl, aryl, aryloxy, halogen, an unsubstituted or substituted $C_4H_4$ chain fused to the benzene radical, alkoxy, haloalkoxy, alkylthio, thiocyanato, cyano, $NO_2$, aralkyloxy,

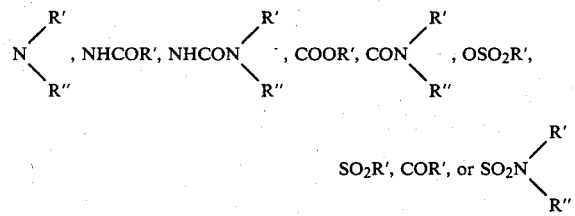

and R' and R'' independently of one another are each hydrogen, alkyl, alkoxy, alkylthio or cycloalkyl or are each phenyl which is unsubstituted or substituted by alkyl, halogen or alkoxy, and n is from 1 to 4, and fungicides containing them.

8 Claims, No Drawings

ACRYLATES, AND FUNGICIDES WHICH CONTAIN THESE COMPOUNDS

The present invention relates to novel acrylates, and fungicides which contain these compounds.

It is known that N-tridecyl-2,6-dimethylmorpholine or its salts, e.g. the acetate, can be used as fungicides (German Pat. Nos. 1,164,152 and 1,173,722). However, the fungicidal action is inadequate in some cases.

We have found that novel acrylates of the formula

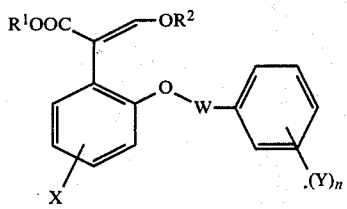

where $R^1$ and $R^2$ independently of one another are each $C_1$–$C_8$-alkyl, X is hydrogen, $C_1$–$C_4$-alkyl, halogen, $C_1$–$C_4$-alkoxy, haloalkyl, cyano or nitro, W is unsubstituted or alkyl-substituted, saturated or unsaturated $C_1$–$C_{10}$-alkylene, Y is hydrogen, alkyl, haloalkyl, alkoxyalkyl, cycloalkyl, aralkyl, aryl, aryloxy, halogen, an unsubstituted or substituted $C_4H_4$ chain fused to the benzene radical, alkoxy, haloalkoxy, alkylthio, thiocyanato, cyano, $NO_2$, aralkyloxy,

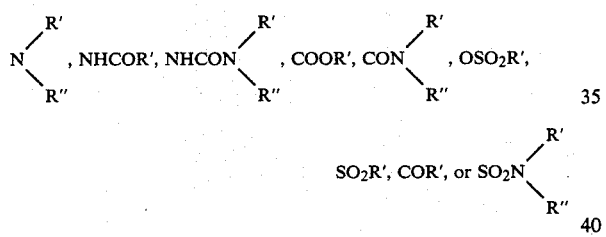

and R' and R" independently of one another are each hydrogen, alkyl, alkoxy, alkylthio or cycloalkyl or are each phenyl which is unsubstituted or substituted by alkyl, halogen or alkoxy, and n is from 1 to 4, have an excellent fungicidal action.

In the general formula, $R^1$ and $R^2$ may each be, for example, straight-chain or branched $C_1$–$C_8$-alkyl (e.g. methyl, ethyl, isopropyl, n-propyl, n-butyl, sec-butyl, tert-butyl, isobutyl, sec-pentyl, n-hexyl, α-ethyl-n-hexyl or n-octyl), X may be, for example, hydrogen, $C_1$–$C_4$-alkyl (e.g. methyl or tert-butyl), halogen (e.g. fluorine, chlorine or bromine), $C_1$–$C_4$-alkoxy (e.g. methoxy or n-butoxy), haloalkyl (e.g. trifluoromethyl), cyano or nitro, W may be, for example, unsubstituted or $C_1$–$C_4$-alkyl-substituted, saturated or unsaturated $C_1$–$C_{10}$-alkylene (e.g. methylene, methylmethylene, dimethylmethylene, propylene, allylene, hexylene, ethylene, methylethylene, methylpropylene, ethylpropylene, butylene, pentylene, methylpentylene, dimethylpropylene, heptylene, ethylbutylene or trimethylpentylene), Y may be, for example, hydrogen, $C_1$–$C_{12}$-alkyl (e.g. methyl, ethyl, tert-butyl or dodecyl), haloalkyl (e.g. trifluoromethyl), $C_1$–$C_4$-alkoxy-$C_1$–$C_4$-alkyl (e.g. methoxymethyl), $C_5$–$C_8$-cycloalkyl (e.g. cyclohexyl), aralkyl (e.g. benzyl, phenethyl), aryl (e.g. phenyl), aryloxy (e.g. phenoxy), halogen (e.g. fluorine, chlorine, bromine or iodine), an unsubstituted or substituted $C_4H_4$ chain which is fused to the benzene ring to form an unsubstituted or substituted naphthyl ring, $C_1$–$C_8$-alkoxy (e.g. isopropoxy or hexyloxy), halo-$C_1$–$C_4$-alkoxy (e.g. 1,1,2,2-tetrafluoroethoxy), $C_1$–$C_4$-alkylthio (e.g. methylthio), thiocyanato, cyano, $NO_2$, aralkyloxy (benzyloxy, phenethyloxy),

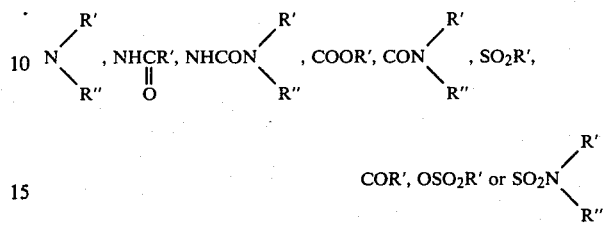

and R' and R" independently of one another are each hydrogen, $C_1$–$C_4$-alkyl (e.g. methyl or ethyl), $C_1$–$C_4$-alkoxy (e.g. methoxy or tert-butoxy), $C_1$–$C_4$-alkylthio (e.g. methylthio), $C_5$–$C_8$-cycloalkyl (e.g. cyclohexyl) or phenyl which is unsubstituted or substituted by $C_1$–$C_4$-alkyl, halogen or $C_1$–$C_4$-alkoxy (e.g. phenyl, 3-chlorophenyl, 4-methylphenyl or 3-methoxyphenyl).

The novel fungicidal acrylates may be obtained as E or Z isomers. The stereoisomers can be separated, for example by column chromatography, or isolated in pure form on the basis of solubility differences. The pure isomers may be converted to the other isomers by conventional methods. Both the pure isomers and the mixtures thereof are embraced by the present invention. Both the isomer mixtures and the pure isomers are suitable for use as fungicides.

The novel compounds can be prepared, for example, by the following process:

A phenylacetate of the general formula

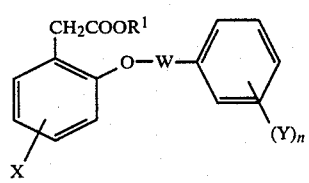

where $R^1$, X, W and $(Y)_n$ have the above meanings, is reacted with methyl formate and sodium hydride in an inert solvent. The resulting compound of the general formula

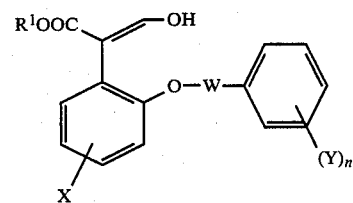

where $R^1$, X, W and $(Y)_n$ have the above meanings, is reacted with an alkylating agent in the presence of a base in an inert solvent (e.g. acetone) to give a novel compound of the general formula

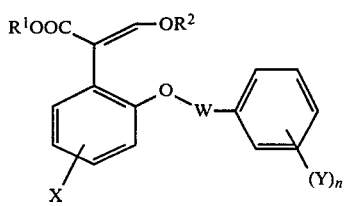

where $R^1$, $R^2$, X, W and $(Y)_n$ have the above meanings (Wislicenus, Liebigs Annalen 413 (1917), 206, and 424 (1921), 215).

The phenylacetates of the general formula

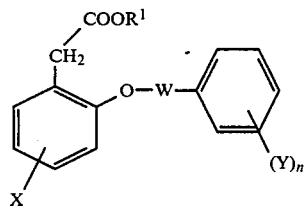

are obtained, for example, by reacting an unsubstituted or substituted 2-hydroxyphenylacetate with a compound of the type

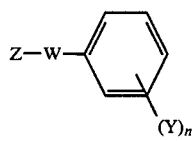

where $R^1$, X, W and $(Y)_n$ have the above meanings and Z is a leaving group, e.g. chlorine, bromine, iodine, mesylate or tosylate (cf. Houben-Weyl, Methoden der organischen Chemie VI/3, 54 et seq. (1965)).

The synthesis of the novel compounds is illustrated below.

Method A

Methyl 2-(benzyloxy)-phenylacetate 15 g of methyl 2-hydroxyphenylacetate are refluxed with 11.4 g of benzyl chloride and 6.2 g of potassium carbonate in 90 ml of absolute methanol for 24 hours. The mixture is filtered, the filtrate is evaporated down, 400 ml of ether are added to the residue, and the solution is washed with water, dried with MgSO₄ and evaporated down. Distillation of the residue at about 200° C. and under 18 mbar gives 15.5 g of pale oil.

NMR spectrum in CDCl₃: 4.97 s for —O—CH₂—O—, 3.6 s for —CH₂COO—, 3.5 s for —COO—CH₃—.

EXAMPLE 1

Methyl α-(2-benzyloxyphenyl)-β-methoxyacrylate 15.5 g of methyl 2-(benzyloxy)-phenylacetate are dissolved in 7 ml of methyl formate and 30 ml of absolute ether, and the solution is slowly added dropwise to a suspension of 1.8 g of sodium hydride in 90 ml of absolute ether, after which the mixture is refluxed for a further 6 hours. The mixture is stirred for 12 hours and then carefully acidified, and the organic phase is washed with water, dried over MgSO₄ and evaporated down to give 13.6 g of a yellow oil (methyl α-formyl-(2-benzyloxyphenyl)-acetate), which is stirred together with 4.1 ml of dimethyl sulfate, 7.5 g of potassium carbonate and 70 ml of acetone for 2 hours. The mixture is then refluxed for ½ an hour and filtered, the filtrate is evaporated down and the residue is taken up in ether, and the solution is then washed with dilute ammonia and several times with water. The ether is stripped off to give 12.6 g of crude methyl α-(2-benzyloxyphenyl)-β-methoxyacrylate (compound No. 1), which can be recrystallized from petroleum ether/chloroform.

| NMR in CDCl₃: | | |
|---|---|---|
| 7.45 | s | 1H |
| 7.3 | bs | 9H |
| 6.8–7.4 | m | |
| 5.03 | S | 2H |
| 3.60 | S | 3H |
| 3.70 | s | 3H |

The compounds below can be prepared in a similar manner:

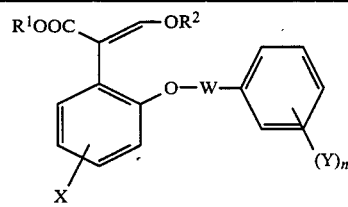

| No. | $R^1$ | $R^2$ | X | W | $(Y)_n$ | M.p. °C./NMR/isomer |
|---|---|---|---|---|---|---|
| 1 | CH₃ | CH₃ | H | —CH₂— | H | 80–82 (E) |
| 2 | CH₃ | CH₃ | H | —CH₂—CH₂— | H | |
| 3 | CH₃ | CH₃ | H | —CH₂—CH=CH— | H | resin |
| 4 | CH₃ | CH₃ | H | —CH₂—CH₂—CH₂— | H | resin |
| 5 | CH₃ | CH₃ | H | —(CH₂)₅— | H | |
| 6 | CH₃ | CH₃ | H | —(CH₂)₇— | H | |
| 7 | CH₃ | CH₃ | H | —(CH₂)₈— | H | |
| 8 | CH₃ | CH₃ | H | —(CH₂)₁₀— | H | |
| 9 | CH₃ | CH₃ | H | —CH(CH₃)— | H | |
| 10 | CH₃ | CH₃ | H | —CH(CH₃)— | 4-Cl | |
| 11 | CH₃ | CH₃ | H | —CH(CH₃)— | 4-OCH₃ | |
| 12 | CH₃ | CH₃ | H | —C(CH₃)₂— | 4-Cl | |

-continued

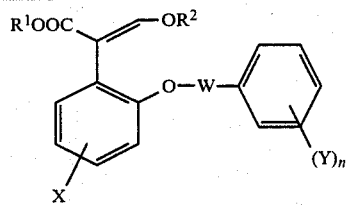

| No. | R¹ | R² | X | W | (Y)$_n$ | M.p. °C./NMR/isomer |
|---|---|---|---|---|---|---|
| 13 | CH$_3$ | CH$_3$ | H | —C(CH$_3$)$_2$— | 3-CF$_3$ | |
| 14 | CH$_3$ | CH$_3$ | H | —CH$_2$CH(CH$_3$)CH$_2$— | H | |
| 15 | CH$_3$ | CH$_3$ | H | —CH$_2$CH(CH$_3$)CH$_2$— | 4-t-C$_4$H$_9$ | |
| 16 | CH$_3$ | CH$_3$ | H | —CH$_2$CH(CH$_3$)CH$_2$— | 4-CH$_3$ | |
| 17 | CH$_3$ | CH$_3$ | H | —CH$_2$CH(CH$_3$)CH$_2$— | 4-Cl | |
| 18 | CH$_3$ | CH$_3$ | H | —CH$_2$CH(CH$_3$)CH$_2$— | 4-F | |
| 19 | CH$_3$ | CH$_3$ | H | —CH$_2$CH(CH$_3$)CH$_2$— | 3,4-(CH$_3$)$_2$ | |
| 20 | CH$_3$ | CH$_3$ | H | —CH(CH$_3$)CH$_2$— | H | |
| 21 | CH$_3$ | CH$_3$ | H | —CH$_2$—CH(CH$_3$)— | H | |
| 22 | CH$_3$ | CH$_3$ | H | —CH$_2$—CH$_2$— | 4-CH$_3$ | |
| 23 | CH$_3$ | CH$_3$ | H | —CH$_2$—CH$_2$— | 4-Cl | |
| 24 | CH$_3$ | CH$_3$ | H | —CH$_2$—(CH=CH)$_2$— | H | |
| 25 | CH$_3$ | CH$_3$ | H | —CH$_2$—C≡C— | H | |
| 26 | CH$_3$ | CH$_3$ | H | —CH$_2$— | 2-Cl | |
| 27 | CH$_3$ | CH$_3$ | H | —CH$_2$— | 2,4-Cl$_2$ | 100–102 (Z), 116 (E) |
| 28 | CH$_3$ | CH$_3$ | H | —CH$_2$— | 3-Cl | 57 (E) |
| 29 | CH$_3$ | CH$_3$ | H | —CH$_2$— | 3,4-Cl$_2$ | 107 (Z), 131 (E) |
| 30 | CH$_3$ | CH$_3$ | H | —CH$_2$— | 4-Cl | |
| 31 | CH$_3$ | CH$_3$ | H | —CH$_2$— | 3,5-Cl$_2$ | |
| 32 | CH$_3$ | CH$_3$ | H | —CH$_2$— | 2,4,5-Cl$_3$ | |
| 33 | CH$_3$ | CH$_3$ | H | —CH$_2$— | 4-Br | 118 (E) |
| 34 | CH$_3$ | CH$_3$ | H | —CH$_2$— | 4-F | 100 (E) |
| 35 | CH$_3$ | CH$_3$ | H | —CH$_2$— | 4-OCH$_3$ | |
| 36 | CH$_3$ | CH$_3$ | H | —CH$_2$— | 4-O—n(C$_4$H$_9$) | |
| 37 | CH$_3$ | CH$_3$ | H | —CH$_2$— | 4-O—t(C$_4$H$_9$) | |
| 38 | CH$_3$ | CH$_3$ | H | —CH$_2$— | 4-CH$_3$ | 71–74 (Z), 94–98 (E) |
| 39 | CH$_3$ | CH$_3$ | H | —CH$_2$— | 2-CH$_3$ | |
| 40 | CH$_3$ | CH$_3$ | H | —CH$_2$— | 3-CH$_3$ | |
| 41 | CH$_3$ | CH$_3$ | H | —CH$_2$— | 4-t-C$_4$H$_9$ | |
| 42 | CH$_3$ | CH$_3$ | H | —CH$_2$— | 4-cyclo-C$_6$H$_{11}$ | |
| 43 | CH$_3$ | CH$_3$ | H | —CH$_2$— | 3-benzyl | |
| 44 | CH$_3$ | CH$_3$ | H | —CH$_2$— | 3-phenoxy | |
| 45 | CH$_3$ | CH$_3$ | H | —CH$_2$— | 4-phenoxy | |
| 46 | CH$_3$ | CH$_3$ | H | —CH$_2$— | 3-CH$_2$OCH$_3$ | |
| 47 | CH$_3$ | CH$_3$ | H | —CH$_2$— | 2-CH$_2$OCH$_3$ | |
| 48 | CH$_3$ | CH$_3$ | H | —CH$_2$— | 3-CF$_3$ | |
| 49 | CH$_3$ | CH$_3$ | H | —CH$_2$— | 4-CF$_3$ | |
| 50 | CH$_3$ | CH$_3$ | H | —CH$_2$— | 3-C$_2$H$_5$ | |
| 51 | CH$_3$ | CH$_3$ | H | —CH$_2$— | 2-OCH$_3$ | |
| 52 | CH$_3$ | CH$_3$ | H | —CH$_2$— | 3-OCH$_3$ | resin (Z) |
| 53 | CH$_3$ | CH$_3$ | H | —CH$_2$— | 4-I | |
| 54 | CH$_3$ | CH$_3$ | H | —CH$_2$— | 3-F | |
| 55 | CH$_3$ | CH$_3$ | H | —CH$_2$— | 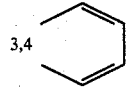 3,4 | |
| 56 | CH$_3$ | CH$_3$ | H | —CH$_2$— | 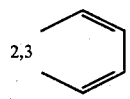 2,3 | |
| 57 | CH$_3$ | CH$_3$ | H | —CH$_2$— | 4-OCHF$_2$ | |
| 58 | CH$_3$ | CH$_3$ | H | —CH$_2$— | 3-OCF$_2$CHF$_2$ | |
| 59 | CH$_3$ | CH$_3$ | H | —CH$_2$— | 4-SCH$_3$ | |
| 60 | CH$_3$ | CH$_3$ | H | —CH$_2$— | 4-CN | resin (E) |
| 61 | CH$_3$ | CH$_3$ | H | —CH$_2$— | 3-CN | |
| 62 | CH$_3$ | CH$_3$ | H | —CH$_2$— | 4-SCN | |
| 63 | CH$_3$ | CH$_3$ | H | —CH$_2$— | 4-N(CH$_3$)$_2$ | |
| 64 | CH$_3$ | CH$_3$ | H | —CH$_2$— | 3-NHCOCH$_3$ | |
| 65 | CH$_3$ | CH$_3$ | H | —CH$_2$— | 3-NHCOOCH$_3$ | |
| 66 | CH$_3$ | CH$_3$ | H | —CH$_2$— | 3-NHCON(CH$_3$)$_2$ | |
| 67 | CH$_3$ | CH$_3$ | H | —CH$_2$— | 4-COOCH$_3$ | |
| 68 | CH$_3$ | CH$_3$ | H | —CH$_2$— | 4-CONHCH$_3$ | |
| 69 | CH$_3$ | CH$_3$ | H | —CH$_2$— | 4-CON(CH$_3$)$_2$ | |
| 70 | CH$_3$ | CH$_3$ | H | —CH$_2$— | 4-SO$_2$CH$_3$ | |
| 71 | CH$_3$ | CH$_3$ | H | —CH$_2$— | 4-phenylsulfonyl | |

-continued

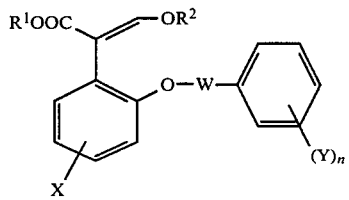

| No. | R¹ | R² | X | W | (Y)$_n$ | M.p. °C./NMR/isomer |
|---|---|---|---|---|---|---|
| 72 | $CH_3$ | $CH_3$ | H | $-CH_2-$ | 3-$COCH_3$ | |
| 73 | $CH_3$ | $CH_3$ | H | $-CH_2-$ | 4-$OSO_2CH_3$ | |
| 74 | $CH_3$ | $CH_3$ | H | $-CH_2-$ | 4-$SO_2N(CH_3)_2$ | |
| 75 | $CH_3$ | $CH_3$ | H | $-CH_2-$ | 4-CONH– 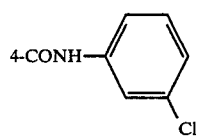 | |
| 76 | $CH_3$ | $CH_3$ | H | $-CH_2-$ | 4-benzoyl | |
| 77 | $C_2H_5$ | $CH_3$ | H | $-CH_2-$ | H | |
| 78 | i-$C_3H_7$ | $CH_3$ | H | $-CH_2-$ | H | |
| 79 | n-$C_6H_{13}$ | $CH_3$ | H | $-CH_2-$ | H | |
| 80 | n-$C_4H_9$ | $CH_3$ | H | $-CH_2-$ | H | |
| 81 | n-$C_3H_7$ | $CH_3$ | H | $-CH_2-$ | H | |
| 82 | s-$C_4H_9$ | $CH_3$ | H | $-CH_2-$ | H | |
| 83 | $CH_3$ | $C_2H_5$ | H | $-CH_2-$ | H | resin (E) |
| 84 | $CH_3$ | i-$C_3H_7$ | H | $-CH_2-$ | H | 73–74 (E) |
| 85 | $CH_3$ | n-$C_6H_{13}$ | H | $-CH_2-$ | H | resin (E) |
| 86 | $CH_3$ | n-$C_3H_7$ | H | $-CH_2-$ | H | |
| 87 | $CH_3$ | s-$C_4H_9$ | H | $-CH_2-$ | H | |
| 88 | $CH_3$ | $CH_3$ | 3-$CH_3$ | $-CH_2-$ | H | |
| 89 | $CH_3$ | $CH_3$ | 4-$CH_3$ | $-Ch_2-$ | H | |
| 90 | $CH_3$ | $CH_3$ | 5-Cl | $-CH_2-$ | H | |
| 91 | $CH_3$ | $CH_3$ | 5-Br | $-CH_2-$ | H | |
| 92 | $CH_3$ | $CH_3$ | 6-Cl | $-CH_2-$ | H | |
| 93 | $CH_3$ | $CH_3$ | 6-$CH_3$ | $-CH_2-$ | H | |
| 94 | $CH_3$ | $CH_3$ | 5-F | $-CH_2-$ | H | |
| 95 | $CH_3$ | $CH_3$ | 5-$CF_3$ | $-CH_2-$ | H | |
| 96 | $CH_3$ | $CH_3$ | H | $-CH_2-$ | 3-$NO_2$ | |
| 97 | $CH_3$ | $CH_3$ | H | $-CH_2-$ | 3-$N(CH_3)_2$ | |
| 98 | $CH_3$ | $CH_3$ | H | $-CH_2CH(CH_3)CH_2-$ | 4-phenoxy | |
| 99 | $CH_3$ | $CH_3$ | H | $-CH_2CH(CH_3)CH_2-$ | 2-F | |
| 100 | $CH_3$ | $CH_3$ | H | $C(CH_3)_2$ | H | |
| 101 | $CH_3$ | $CH_3$ | H | $CH_2C(CH_3)_2$ | H | |
| 102 | $CH_3$ | $CH_3$ | H | $CH(CH_3)_2$ | 2,5$(CH_3)_2$ | |
| 103 | $CH_3$ | $CH_3$ | H | $-CH_2-$ | 4$NO_2$ | |
| 104 | $CH_3$ | $CH_3$ | H | $-CH_2-$ | 2Cl,6F | |
| 105 | $CH_3$ | $CH_3$ | H | $-CH_2-$ | 2,3,6(Cl)$_3$ | 100 (Z), 90 (E) |
| 106 | $CH_3$ | $CH_3$ | H | $-CH_2-$ | 3,4$(CH_3)_2$ | |
| 107 | $CH_3$ | $CH_3$ | H | $-CH_2-$ | 2-$CH_3$,4t-$C_4H_9$ | |
| 108 | $CH_3$ | $CH_3$ | H | $-CH_2-$ | 2,4$(CH_3)_2$ | 79 (E) |
| 109 | $CH_3$ | $CH_3$ | H | $-CH_2-$ | 2-$NO_2$ | |
| 110 | $CH_3$ | $CH_3$ | H | $-CH_2-$ | 4-$C_{12}H_{25}$ | |
| 111 | $CH_3$ | $CH_3$ | H | $-CH_2-$ | 4-$C_2H_5$ | |
| 112 | $CH_3$ | $CH_3$ | H | $-CH_2-$ | 3,4,5$(OCH_3)_3$ | |
| 113 | $CH_3$ | $CH_3$ | H | $-CH_2-$ | 2,5$(CH_3)_2$ | |
| 114 | $CH_3$ | $CH_3$ | H | $-CH_2-$ | 2-F | resin (Z) |
| 115 | $CH_3$ | $CH_3$ | H | $-CH_2-$ | 2CN | |
| 116 | $CH_3$ | $CH_3$ | H | $-CH_2-$ | 2,6-$Cl_2$ | 83–85 (Z) |
| 117 | $CH_3$ | $CH_3$ | H | $-CH_2-$ | 2-Cl,6CN | |
| 118 | $CH_3$ | $CH_3$ | H | $-CH_2-$ | 2-Cl,4$NO_2$ | |
| 119 | $CH_3$ | $CH_3$ | H | $-CH_2-$ | 2,4$(NO_2)_2$ | |
| 120 | $CH_3$ | $CH_3$ | H | $(CH_2)_5$ | 4-Cl | |
| 121 | $CH_3$ | n-$C_4H_9$ | H | $-CH_2-$ | H | 73–74 (E) |
| 122 | $CH_3$ | $CH_3$ | H | $-CH_2-$ | 3-benzyloxy | |
| 123 | $CH_3$ | $CH_3$ | H | $-CH_2-$ | 3-phenethyl | |
| 124 | $CH_3$ | $CH_3$ | H | $-CH_2-$ | 4-benzyloxy | |
| 125 | $CH_3$ | $CH_3$ | H | $-CH_2-$ | 4-phenethyl | |
| 126 | $CH_3$ | $CH_3$ | H | $-CH_2-$ | 3-phenethyloxy | |
| 127 | $CH_3$ | $CH_3$ | H | $-CH_2-$ | 4-phenethyloxy | |

In general terms, the novel compounds are very effective against a broad spectrum of phytopathogenic fungi, in particular those from the class consisting of the Ascomycetes, Phycomycetes and Basidiomycetes. Some of them have a systemic action and can be used as foliar and soil fungicides.

The fungicidal compounds are of particular interest for controlling a large number of fungi in various crops or their seeds, in particular wheat, rye, barley, oats, rice, corn, cotton, soybean, coffee, sugar cane, fruit and ornamentals in horticulture, in viticulture, and in vegetables, such as cucumbers, beans and Cucurbitaceae.

The novel compounds are particularly useful for controlling the following plant diseases:
*Erysiphe graminis* in cereals,
*Erysiphe cichoracearum* and *Sphaerotheca fuliginea* in Cucurbitaceae,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
*Septoria nodorum* in wheat,
*Pyrenophora teres* in barley,
*Botrytis cinerea* (gray mold) in strawberries and vines,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Alternaria solani in potatoes and tomatoes,*
*Plasmopara viticola in vines,* and
Fusarium and Verticillium species in various plants.

The compounds are applied by spraying or dusting plants with the active ingredients, or treating the seeds of the plants with the active ingredients. They are applied before or after infection of the plants or seeds by the fungi.

The novel substances can be converted to the conventional formulations, such as solutions, emulsions, suspensions, dusts, powders, pastes and granules. The application forms depend entirely on the pruposes for which they are intended; they should at all events ensure a fine and uniform distribution of the active substance. The formulations are produced in a known manner, for example by extending the active ingredient with solvents and/or carriers, with or without the use of emulsifiers and dispersants; if water is used as a diluent, it is also possible to employ other, organic solvents as auxiliary solvents. Suitable assistants for this purpose are essentially solvents, such as aromatics (e.g. xylene or benzene), chlorinated aromatics (e.g. chlorobenzenes), paraffins (e.g. oil fractions), alcohols (e.g. methanol or butanol), ketones (e.g. cyclohexanone), amines (e.g. ethanolamine or dimethylformamide) and water; carriers, such as ground natural minerals (kaolins, aluminas, talc or chalk) and ground synthetic minerals (e.g. highly disperse silica or silicates); emulsifiers, such as nonionic and anionic emulsifiers (e.g. polyoxyethylene fatty alcohol ethers, alkylsulfonates and arylsulfonates) and dispersants, such as lignin, sulfite waste liquors and methylcellulose.

The fungicides generally contain from 0.1 to 95, preferably from 0.5 to 90, % by weight of active ingredient.

The application rates are from 0.05 to 3 kg or more of active ingredient per ha, depending on the type of effect desired. The novel compounds may also be employed in material protection, inter alia for controlling wood-destroying fungi, such as *Coniophora puteana* and *Polystictus versicolor.* The novel active ingredients can also be used as fungicidal components of oily wood preservatives for protecting wood against wood-discoloring fungi. They are used by treating, for example impregnating or painting, the wood with these agents.

The agents and the ready-to-use formulations prepared from them, such as solutions, emulsions, suspensions, powders, dusts, pastes or granules, are applied in a conventional manner, for example by spraying, atomizing, dusting, scattering, dressing or watering.

Examples of such formulations are:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzensulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 1 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be present together with other active ingredients, for example herbicides, insecticides, growth regulators and fungicides, or may futhermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
  ferric dimethyldithiocarbamate,
  zinc dimethyldithiocarbamate,
  zinc ethylenebisdithiocarbamate,
  manganese ethylenebisdithiocarbamate,
  manganese zinc ethylenediaminebisdithiocarbamate,
  tetramethylthiuram disulfides,
  ammonia complex of zinc N,N'-ethylenebisdithiocarbamate,
  ammonia complex of zinc N,N'-propylenebisdithiocarbamate,
  zinc N,N'-propylenebisdithiocarbamate and
  N,N'-polypropylenebis(thiocarbamyl) disulfide;
nitro derivatives, such as
  dinitro(1-methylheptyl)-phenyl crotonate,
  2-sec-butyl-4,6-dinitrophenyl 3,3-dimethylacrylate,
  2-sec-butyl-4,6-dinitrophenyl isopropylcarbonate and
  diisopropyl 5-nitroisophthalate;
heterocyclic substances, such as
  2-heptadecylimidazol-2-yl acetate,
  2,4-dichloro-6-(o-chloroanilino)-s-triazine,
  0,0-diethyl phthalimidophosphonothioate,
  5-amino-1-[bis-(dimethylamino)-phosphinyl]-3-phenyl-1,2,4-triazole,
  2,3-dicyano-1,4-dithiaanthraquinone,
  2-thio-1,3-dithio[4,5-b]quinoxaline,
  methyl 1-(butylcarbamyl)-2-benzimidazolecarbamate,
  2-methoxycarbonylaminobenzimidazole,
  2-(fur-2-yl)-benzimidazole,
  2-(thiazol-4-yl)benzimidazole,
  N-(1,1,2,2-tetrachloroethylthio)-tetrahydrophthalimide,
  N-trichloromethylthiotetrahydrophthalimide,
  N-trichloromethylthiophthalimide,
  N-dichlorofluoromethylthio-N',N'-dimethyl-N-phenylsulfuric acid diamide,
  5-ethoxy-3-trichloromethyl-1,2,3-thiadiazole,
  2-thiocyanatomethylthiobenzothiazole,
  1,4-dichloro-2,5-dimethoxybenzene,
  4-(2-chlorophenylhydrazono)-3-methyl-5-isoxazolone,
  2-thiopyridine 1-oxide,
  8-hydroxyquinoline and its copper salt,
  2,3-dihydro-5-carboxanilido-6-methyl-1,4-oxathiin,
  2,3-dihydro-5-carboxanilido-6-methyl-1,4-oxathiin 4,4-dioxide,
  2-methyl-5,6-dihydro-4H-pyran-3-carboxanilide,
  2-methylfuran-3-carboxanilide,
  2,5-dimethylfuran-3-carboxanilide,
  2,4,5-trimethylfuran-3-carboxanilide,
  2,5-dimethyl-N-cyclohexylfuran-3-carboxamide,
  N-cyclohexyl-N-methoxy-2,5-dimethylfuran-3-carboxamide,
  2-methylbenzanilide,
  2-iodobenzanilide,
  N-formyl-N-morpholine-2,2,2-trichloroethylacetal, piperazine-1,4-diylbis-(1-(2,2,2-trichloroethyl)-formamide),
  1-(3,4-dichloroanilino)-1-formylamino-2,2,2-trichloroethane,
  2,6-dimethyl-N-tridecylmorpholine and its salts,
  2,6-dimethyl-N-cyclododecylmorpholine and its salts,
  N-[3-(p-tert.-butylphenyl)-2-methylpropyl]-cis-2,6-dimethylmorpholine,
  N-[3-p-tert.-butylphenyl]-2-methylpropyl]-piperidine,
  1-[2-(2,4-dichlorophenyl)-4-ethyl-1,3-dioxolan-2-ylethyl]-1H-1,2,4-triazole,
  1-[2-(2,4-dichlorophenyl)-4-n-propyl-1,3-dioxolan-2-yl-ethyl]-1H-1,2,4-triazole,
  N-(n-propyl)-N-(2,4,6-trichlorophenoxyethyl)-N'-imidazolyl-urea,
  1-(4-chlorophenoxy)-3,3-dimethyl-1-(1H-1,2,4-triazol-1-yl)-butan-2-one,
  1-(4-chlorophenoxy)-3,3-dimethyl-1-(1H-1,2,4-triazol-1-yl)butan-2-ol,
  α-(2-chlorophenyl)-α-(4-chlorophenyl)-5-pyrimidinemethanol,
  5-butyl-2-dimethylamino-4-hydroxy-6-methylpyrimidine,
  bis-(p-chlorophenyl)-3-pyridinemethanol,
  1,2-bis-(3-ethoxycarbonyl-2-thioureido)-benzene,
  1,2-bis-(3-methoxycarbonyl-2-thioureido)-benzene,
and various fungicides, such as
  dodecylguanidine acetate,
  3-[3-(3,5-dimethyl-2-oxycyclohexyl)-2-hydroxyethyl]-glutaramide,
  hexachlorobenzene,
  DL-methyl-N-(2,6-dimethylphenyl)-N-fur-2-yl alanate,
  methyl DL-N-(2,6-dimethylphenyl)-N-(2'-methoxyacetyl)-alanate,
  N-(2,6-dimethylphenyl)-N-chloroacetyl-DL-2-aminobutyrolactone,
  methyl DL-N-(2,6-dimethylphenyl)-N-(phenylacetyl)-alanate,
  5-methyl-5-vinyl-3-(3,5-dichlorophenyl)-2,4-dioxo-1,3-oxazolidine,
  3-[3,5-dichlorophenyl]-5-methyl-5-methoxymethyl-1,3-oxazolidine-2,4-dione,
  3-(3,5-dichlorophenyl)-1-isopropylcarbamylhydantoin,
  N-(3,5-dichlorophenyl)-1,2-dimethylcyclopropane-1,2-dicarboximide,
  2-cyano-[N-(ethylaminocarbonyl)-2-methoximino]-acetamide,
  1-[2-(2,4-dichlorophenyl)-pentyl]-1H-1,2,4-triazole and
  2,4-difluoro-α-(1H-1,2,4-triazol-1-ylmethyl)-benzhydryl alcohol
  N-(n-propyl)-N-(2,4,6-trichlorophenoxyethyl)-N'-imidazolylurea.

For the tests below, the known active ingredients N-tridecyl-2,6-dimethylmorpholine (A) and its acetate (B) were used as comparisons.

USE EXAMPLE 1

Action on powdery mildew of wheat

Leaves of pot-grown wheat seedlings of the Frühgold variety were sprayed with aqueous spray liquors containing (dry basis) 80% of active ingredient and 20% of emulsifier, and, 24 hours after the spray coating had dried on, the leaves were dusted with oidia (spores) of powdery mildew of wheat (*Erysiphe graminis* var.

*tritici*). The test plants were then placed in a greenhouse at from 20° to 22° C. and from 75 to 80% relative humidity. After 7 days, the extent of powdery mildew development was determined.

The results show that, when used as a liquor containing the active ingredients in concentrations of 0.025, 0.006 and 0.0015 wt%, compounds nos. 1, 28 and 114 have a better fungicidal action (90%) than known active ingredients A and B (50%).

USE EXAMPLE 2

Action on barley mildew after seed dressing

Barley seed of the "Asse" variety was treated with the stated amounts of a seed dressing consisting of 40% active ingredient and 60% solid carrier. Pots were filled with steamed soil, and 10 seeds sown into each pot. After 8 days in the greenhouse at 20° to 22° C., the first leaf of the young barley plants had fully developed. They were then inoculated with spores of barley mildew (*Erysiphe graminis* f. sp. *hordei*). The plants were then cultivated for a further 8 days in the greenhouse at from 20° to 22° C. and a relative humidity of 70 to 80%. The extent of mildew spread was then determined.

The results show that seed dressing mixtures containing 0.3, 0.2, 0.1 and 0.005% of active ingredient no. 1 have a good fungicidal action (100%).

USE EXAMPLE 3

Action of *Pyrenophora teres*

Leaves of pot-grown barley seedlings of the Asse variety were sprayed, at the two-leaf stage, to runoff with aqueous spray liquors containing (dry basis) 80% of active ingredient and 20% of emulsifier. On the following day, the dried plants were inoculated with an aqueous spore suspension of *Pyrenophora teres*, and cultivated further for 7 days at from 17° to 19° C. and 95% relative humidity. The extent of fungal infestation was then determined.

The results show that, when used as a liquor containing the active ingredients in a concentration of 0.05%, compounds nos. 1, 4, 28, 52 and 114 have a better fungicidal action (90%) than prior art active ingredient A (60%).

USE EXAMPLE 4

Action on apple scab

Young leaves of pot-grown apple seedlings of the "Golden Delicious" variety were sprayed to runoff with aqueous spray liquors containing (dry basis) 80% of active ingredient and 20% of emulsifier. After the sprayed-on layer had dried, the plants were sprayed with a spore suspension of apple scab (*Venturia inaequalis*). The inoculated plants were then set up in a climatic cabinet for 18 days at 20° to 22° C. and a relative humidity of 95%. The extent of fungus spread on the leaves was then determined.

The results show that active ingredient no. 1, when applied as a 0.0075 and 0.00375% spray liquor, had a good fungicidal action (97%).

USE EXAMPLE 5

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that active ingredients nos. 1, 3, 4, 28, 33, 52, 60, 114 and 116, applied as 0.05% spray liquors, had a better fungicidal action (97%) than prior art active ingredient A (50%).

We claim:

1. An acrylate of the formula

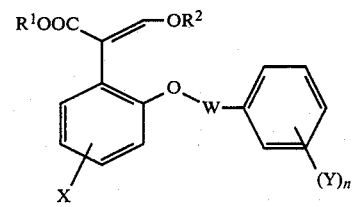

where $R^1$ and $R^2$ independently of one another are each $C_1$–$C_8$-alkyl, X is hydrogen, $C_1$–$C_4$-alkyl, halogen, $C_1$–$C_4$-alkoxy, haloalkyl, cyano or nitro, W is unsubstituted or alkyl-substituted, saturated or unsaturated $C_1$–$C_{10}$-alkylene, Y is hydrogen, alkyl, haloalkyl, alkoxyalkyl, cycloalkyl, aralkyl, aryl, aryloxy, halogen, an unsubstituted or substituted $C_4H_4$ chain fused to the benzene radical, alkoxy, haloalkoxy, alkylthio, thiocyanato, cyano, $NO_2$, aralkyloxy,

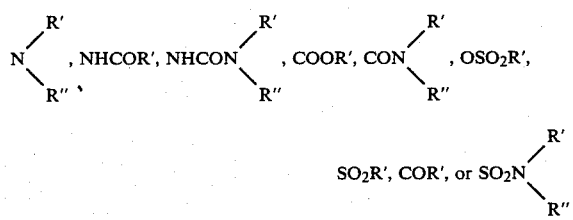

and R' and R" independently of one another are each hydrogen, alkyl, alkoxy, alkylthio or cycloalkyl or are each phenyl which is unsubstituted or substituted by alkyl, halogen or alkoxy, and n is from 1 to 4.

2. A fungicide containing a solid or liquid carrier and an effective amount of an acrylate of the formula

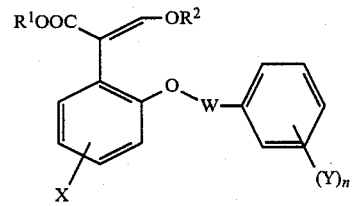

where $R^1$ and $R^2$ independently of one another are each $C_1$–$C_8$-alkyl, X is hydrogen, $C_1$–$C_4$-alkyl, halogen, $C_1$–$C_4$-alkoxy, haloalkyl, cyano or nitro, W is unsubstituted or alkyl-substituted, saturated or unsaturated $C_1$–$C_{10}$-alkylene, Y is hydrogen, alkyl, haloalkyl, alkoxyalkyl, cycloalkyl, aralkyl, aryl, aryloxy, halogen, an unsubstituted or substituted C₄H₄ chain fused to the benzene radical, alkoxy, haloalkoxy, alkylthio, thiocyanato, cyano, NO₂, aralkyloxy,

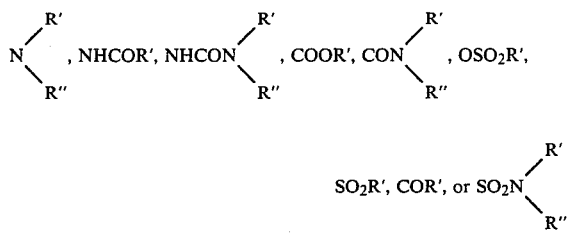

and R' and R" independently of one another are each hydrogen, alkyl, alkoxy, alkylthio or cycloalkyl or are each phenyl which is unsubstituted or substituted by alkyl, halogen or alkoxy, and n is from 1 to 4.

3. Methyl α-(2-benzyloxyphenyl)-β-methoxyacrylate.

4. A fungicide containing a solid or liquid carrier and methyl α-(2-benzyloxyphenyl)-β-methoxyacrylate.

5. A process for combatting fungi, wherein the fungi or the materials, plants, seed or the soil threatened by fungus attack are treated with a fungicidally effective amount of a compound as set forth in claim 1.

6. An acrylate as defined in claim 1, wherein W is methylmethylene, propylene, allylene, hexylene, ethylene, methylethylene, methylpropylene, ethylpropylene, butylene, pentylene, methylpentylene, dimethylpropylene, heptylene, ethylbutylene or trimethylpentylene.

7. A fungicide as defined in claim 2, wherein W is methylmethylene, propylene, allylene, hexylene, ethylene, methylethylene, methylpropylene, ethylpropylene, butylene, pentylene, methylpentylene, dimethylpropylene, heptylene, ethylbutylene or trimethylpentylene.

8. A process as defined in claim 5, wherein the active compound is as defined in claim 6.

* * * * *

Adverse Decisions In Interference

Patent No. 4,709,078, Ulrich Schirmer, Stefan Karbach, Ernst-Heinrich Pommer, Eberhard Ammermann, Wolfgang Steglich, Barbara A. M. Schwalge, Timm Anke, ACRYLATES, AND FUNGICIDES WHICH CONTAIN THESE COMPOUNDS, Interference No. 102,848, final judgment adverse to the patentees rendered April 16, 1998, as to claims 1-8.

*(Official Gazette July 7, 1998)*